United States Patent [19]

Ishikawa

[11] Patent Number: 4,610,987
[45] Date of Patent: * Sep. 9, 1986

[54] IMIDAZOQUINAZOLIN-2-ONE COMPOUNDS

[75] Inventor: Fumiyoshi Ishikawa, Tokyo, Japan

[73] Assignee: Daiichi Seiyaku Co., Ltd., Tokyo, Japan

[*] Notice: The portion of the term of this patent subsequent to Jun. 24, 2003 has been disclaimed.

[21] Appl. No.: 631,417

[22] Filed: Jul. 16, 1984

[30] Foreign Application Priority Data

Jul. 14, 1983 [JP] Japan .................... 58-128173

[51] Int. Cl.[4] ............... A61K 31/505; C07D 487/04
[52] U.S. Cl. .................................. 514/239; 514/267; 544/115; 544/250
[58] Field of Search .................... 424/251, 248.57; 544/250, 115; 514/267, 239

[56] References Cited

U.S. PATENT DOCUMENTS

| | | |
|---|---|---|
| 3,932,407 | 1/1976 | Beverung, Jr. et al. ............. 544/250 |
| 3,983,119 | 9/1976 | Beverung, Jr. et al. ............. 544/250 |
| 3,983,120 | 9/1976 | Beverung, Jr. et al. ............. 544/250 |
| 4,208,521 | 6/1980 | Crenshaw et al. ................... 544/250 |
| 4,256,748 | 3/1981 | Chodnekar et al. ................. 424/251 |
| 4,455,311 | 6/1984 | Kienzle ................................ 424/251 |

Primary Examiner—Donald G. Daus
Assistant Examiner—D. G. Rivers
Attorney, Agent, or Firm—Sughrue, Mion, Zinn, Macpeak, and Seas

[57] ABSTRACT

Imidazoquinazolin-2-one compounds having platelet aggregation inhibitory activity is disclosed. These compounds have high water-solubility and reduced influences on the circulatory system and are useful for treatment and prophylaxis of intravascular thromboembolism and temporary ischemia as well as prevention of thrombus upon use of prosthetic apparatus.

8 Claims, No Drawings

IMIDAZOQUINAZOLIN-2-ONE COMPOUNDS

FIELD OF THE INVENTION

This invention relates to novel compounds having a blood platelet aggregation inhibitory activity and salts thereof. More particularly, this invention relates to an imidazoquinazolin-2-one compound represented by the formula (I):

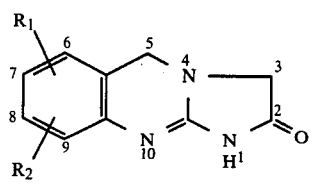

wherein $R_1$ represents a di-lower alkylamino group, a cyclic amino group or a substituted cyclic amino group; and $R_2$ represents a hydrogen atom, a halogen atom, a lower alkyl group or a lower alkoxy group, with proviso that the case wherein $R_1$ is a 7-piperidino group and $R_2$ is a hydrogen atom is excluded, and a pharmaceutically acceptable salt thereof.

BACKGROUND OF THE INVENTION

Known compounds having the same skeleton as the compound of the above-described formula (I) and also exhibiting a blood platelet aggregation inhibitory activity include a series of compounds disclosed in Japanese Patent Publication No. 23994/81 corresponding to U.S. Pat. No. 3,932,407 and U.S. Pat. No. 4,641,718.

However, among the above-described known compounds, those having excellent anti-platelet aggregation activity are all sparingly soluble in water and are not, therefore, suitable for parenteral administration. Further, these compounds are characterized by their potent hypotensive activity, and such a hypotensive activity rather exerts a harmful influence on the circulatory systems when applied in the therapy of thromboembolia making use of their platelet aggregation inhibitory activity.

Also, U.S. Pat. No. 4,256,748 discloses imidazo[2,1-b]quinazolin-2(3H)-ones which are useful for treating and prophylaxis of cardiac insufficiency and cardiac failure, but these compounds have a substituent such as an alkyl group at the 3-position of the imidazo[2,1-b]quinazolin skeleton and their activity is different from that of the compound of this invention.

SUMMARY OF THE INVENTION

The present inventors have conducted extensive studies to eliminate the above-described disadvantages possessed by the known compounds, i.e., sparing water-solubility and the adverse influence on the circulatory system and, as a result, found that the compounds represented by the formula (I) are highly soluble in water to exhibit high activity even through parenteral administration and also has but relatively slight influence on the circulatory system while retaining a potent platelet aggregation inhibitory activity, when compared with the above-described known compounds. It was also found that the compounds (I) of the present invention possess an activity to inhibit platelet aggregation induced by cancer cells, thereby to inhibit metastasis of cancers.

DETAILED DESCRIPTION OF THE INVENTION

The compounds represented by the formula (I) may be present in the form of tautomers as shown by the following formulae (Ia) and (Ib), but it should be understood that they are also within the scope of this invention.

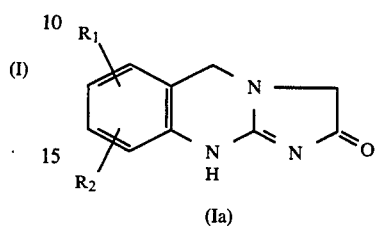

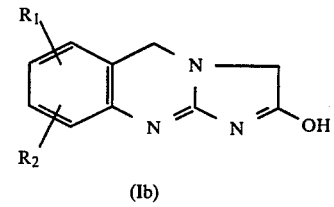

wherein $R_1$ and $R_2$ are as defined above.

The present invention will be described in detail referring only to the formula (I) for the sake of convenience but not for limitation.

In the above-described formula (I), the lower alkyl moiety in the di-lower alkylamino group as represented by $R_1$ contains 1 to 6 carbon atoms, preferably 1 to 2 carbon atoms. The lower alkyl group as represented by $R_2$ contains 1 to 6 carbon atoms, preferably 1 to 2 carbon atoms. The lower alkoxy group as represented by $R_2$ contains 1 to 6 carbon atoms, preferably 1 to 2 carbon atoms.

The cyclic amino group as represented by $R_1$ is composed of a nitrogen atom and a carbon atom, and may further contain one hetero atom, such as a nitrogen atom or an oxygen atom. Such a cyclic amino group includes, for example, a 1-pyrrolidinyl group, a 1-piperidinyl group, a 1-piperazinyl group, a 4-morpholinyl group, etc.

Further, the substituted cyclic amino group includes the above-described cyclic amino group substituted with one or more lower alkyl groups having 1 to 2 carbon atoms, such as a 4-methyl-1-piperazinyl group, a 4-methyl-1-piperidinyl group, a 2-methyl-1-piperidinyl group, a 3,5-dimethyl-1-piperidinyl group, etc.

The compounds (I) of this invention can be used in the form of an acid addition salt thereof with a physiologically non-toxic acid such as hydrochloride, sulfate, phosphate, alkyl- or arylsulfonate, fumarate, maleate, succinate, citrate, and other salts formed with an acid commonly employed in the art, with a hydrochloride being preferred.

The compounds of this invention possess a platelet aggregation inhibitory activity and are, therefore, useful for treatment and propylaxis of intravascular thromboembolia, prophylaxis of temporary ischemia, prevention of formation of thrombus upon use of prosthetic apparatus such as artificial heart and artificial kidney, etc.

The above set forth excellent activities of the compounds of this invention will be illustrated by way of Test Examples. In these Test Examples, comparisons were made with 6-methyl-1,2,3,5-tetrahydroimidazo[2,1-b]quinazolin-2-one hydrochloride (BL-3459) that was reported as outstandingly excellent compound in the aforesaid Japanese Patent Publication No. 23994/81 (U.S. Pat. No. 3,932,407), 7-amino-1,2,3,5-tetrahydroimidazo[2,1-b]quinazolin-2-one dihydrochloride (BL-7-NH$_2$) which has a similar basic residue as that of the compounds of this invention and also is described in the same Japanese Patent Publication, and 6,7-dichloro-1,2,3,5-tetrahydro[2,1-b]quinazolin-2-one (BL-4162) that is reported in U.S. Pat. No. 4,641,718 as an outstandingly excellent compound.

TEST EXAMPLE 1

Solubility Test

TABLE 1

| Test Compound | Water-Solubility (mg/ml) | |
|---|---|---|
| | Tap Water* | Water at pH 4 |
| Compound of Example 21 (dihydrochloride) | above 100 | 0.18 |
| BL-3459 (HCl Salt) | below 0.1 | below 0.01 |
| BL-4162 (HCl Salt) | below 0.01 | below 0.01 |

Note:
*An aqueous solution of each test compound showed a pH of about 2.

As shown in Table 1 above, it was revealed that the compound of the present invention is highly water-soluble and also has a sufficient solubility even in water having a pH value used for parenteral preparations in view of the potency of anti-platelet aggregation activity hereinafter described. Therefore, the compound of the present invention is superior to the comparative compounds (BL-3459 and BL-4162).

TEST EXAMPLE 2

Test of Platelet Aggregation Inhibition (in vitro)

The test was performed as follows in accordance with the method of Ashida et al, *Thrombosis and Haemostasis*, Vol. 40, 542 (1979).

Blood was taken by puncture from the heart of a Wistar Imamichi rat under anesthesia with pentobarbital into a syringe containing 1/10 volume of a 3.13% aqueous solution of sodium citrate dihydrate, and the citrated blood was centrifuged to obtain a platelet-rich plasma (PRP). In the same manner, citrated blood was collected from the vein of a healthy human who had not taken aspirin or any other anti-inflammatory agent since before 10 days, followed by centrifugation to obtain PRP. 5 μl of each test compound was added to 0.445 ml of each of these PRP samples, and the system was warmed at 30° C. for 1 minute. 50 μl of an aggregation inducer (ADP or collagen) was then added thereto, and platelet aggregation was determined according to the method of Born, *Nature*, Vol. 194, 927 (1962). The inhibitory activity of platelet aggregation was expressed in terms of 50% inhibition concentration, and the results obtained are shown in Table 2.

Test of Platelet Aggregation Inhibition (ex vivo, p.o.)

Each test compound was dissolved or suspended in a 0.5% Tween 80 aqueous solution and orally administered to 5 Wistar Imamichi rats (body weight: about 260 g) per group which had been deprived of food overnight at a dose of 10 mg/Kg. One hour later, citrated blood was taken from the heart, and platelet aggregation was determined in the same manner as described in the in vitro test. The inhibitory activity was compared with that of control and expressed in terms of percent inhibition. The results obtained are also shown in Table 2.

TABLE 2

| | Platelet Aggregation Inhibitory Activity | | | | |
|---|---|---|---|---|---|
| | | in vitro ($IC_{50}$: μM) | | ex vivo (% inhib.) | |
| Test Compound | Origin of Blood | Collagen | ADP | Collagen | ADP |
| Compound of: | | | | | |
| Example 2 | rat | 1.5 | 2.7 | | |
| Example 5 | " | 1.7 | 2.0 | | |
| Example 9 | " | 1.2 | 7.9 | 32 | 25 |
| Example 15 | " | 0.44 | 1.1 | 49* | 28* |
| Example 16 | " | 0.46 | 0.4 | 76** | 34** |
| Example 16 | human | | 12.5 | | |
| Example 17 | rat | 0.10 | 0.36 | 68** | 47** |
| Example 18 | " | 0.58 | 5.4 | | |
| Example 22 | " | 1.2 | 7.0 | 86*** | 64** |
| Example 23 | " | 1.3 | 5.6 | 70* | 25* |
| Example 26 | " | 1.9 | 2.6 | | |
| Example 28 | " | 2.0 | 5.0 | | |
| Example 21 | " | 1.4 | 5.4 | 48* | 29** |
| Example 21 | human | | 7.2 | | |
| BL-3459 | rat | 0.76 | 5.0 | 54 | 31 |
| | human | | 1.7 | | |
| BL-4162 | rat | 0.02 | 0.8 | 53 | 8 |
| | human | | 1.2 | | |
| BL-7-NH$_2$ | rat | 16 | 170 | | |
| | human | | 50 | | |

Note:
*P < 0.05
**P < 0.01
***P < 0.001

As is apparent from the results shown in Table 2 above, the compounds of the present invention showed a significant aggregation inhibitory activity in either ADP- or collagen-induced aggregation, whereas the activity of the comparative compounds (BL-3459 & BL-4162), though somewhat displayed, widely varied depending on the individual animal and, therefore, cannot be regarded significant. This proves that the compounds of the present invention produce a reliable effect when orally administered to animals.

TEST EXAMPLE 3

Test of Platelet Aggregation Inhibition (ex vivo; i.v.)

As test animals, 5 to 6 Wistar Imamichi rats (body weight: about 260 g) that had been allowed food and water ad libitum were used per group. The test compound was dissolved in a physiological saline solution and continuously injected over a period of 10 or 15 minutes to the rats under anesthesia with pentobarbital through the femoral vein. Immediately after completion of the administration, citrated blood was collected from the heart, and platelet aggregation was determined in the same manner as in the test in vitro in Test Example 2. The results obtained are shown in Table 3 below.

TABLE 3

| Test Compound | Dose (/Kg/min) | Time of Admin. (min) | Percent Inhibition (%) | |
|---|---|---|---|---|
| | | | ADP | Collagen |
| Compound of: | | | | |
| Example 8 | 1.0 mg | 10 | 16.5 | 48.5* |
| Example 22 | 1.0 mg | 10 | 23.5* | 100** |

TABLE 3-continued

| Test Compound | Dose (/Kg/min) | Time of Admin. (min) | Percent Inhibition (%) ADP | Collagen |
|---|---|---|---|---|
| Example 21 | 67 μg | 15 | 23* | 71* |

Note:
*P < 0.05
**P < 0.01

As is apparent from Tables 2 and 3, the compounds of this invention exhibit potent platelet aggregation inhibitory activity and are, therefore, excellent an antithrombotic agents. Further, it was confirmed that a part of the compounds according to the present invention are particularly characterized by their high water-solubility and possibility of parenteral administration in the state of an aqueous solution, especially possibility of continuous intravenous administration, to exhibit markedly high activity.

In particular, in the therapy of acute thromboembolism, it is usually impossible to give drugs to patients through oral administration since many of them have attacks of unconsciousness, and quick onset and long duration of drugs are required. Hence, it has now been proved that the compounds of this invention are extremely excellent from the fact that many compounds having platelet aggregation inhibitory activity are known but none of them exerts such kind of platelet aggregation inhibitory activity through intravenous administration.

Further, the compound having a basic residue (BL-7-NH$_2$) of a series of compounds disclosed in Japanese Patent Publication No. 23994/81 (U.S. Pat. No. 3,932,407) scarecely exhibited platelet aggregation inhibitory activity.

In addition, it was also revealed that the compounds of the present invention inhibit platelet aggregation induced by certain cancer cells. It is known nowadays that platelet aggregation plays an important role in metastasis of cancers. Particularly, it is known that platelet aggregation is induced by the cancer cells taken from B16 melanoma (B16) or Lewis lung cancer (3LL) having been successively implanted to a C57BL/6 male mouse as described in *Invarsion and Metastasis*, Vol. 2, 289 (1982) by N. Tanaka et al. The effect of the compounds of this invention to inhibit the above-described cancer cell-induced platelet aggregation was tested as follows.

TEST EXAMPLE 4

Cell suspensions of B16 or 3LL were prepared according to the method of Tanaka et al, *Invarsion and Metastasis*, Vol. 2, 289 (1982). A platelet-rich-plasma was prepared from a C57BL/6 mouse in the same manner as described in the in vitro test of Test Example 2. 5 μl of the test compound was added to 0.445 ml of the PRP, and 30 seconds later, 50 μl of the cell suspension was added thereto. Platelet aggregation of the sample system was determined according to the method of Born, and the platelet aggregation inhibitory activity was expressed by the following scale:

+: Aggregation was observed.
±: Aggregation was partially inhibited.
−: No aggregation was observed.

The results obtained are shown in Table 4.

TABLE 4

| | Inhibition on Platelet Aggregation Induced by Cancer Cells (in vitro) | | | | | | | | | |
|---|---|---|---|---|---|---|---|---|---|---|
| | B16 Sample Concn. (μM) | | | | | 3LL Sample Concn. (μM) | | | | |
| Test Compound | 0 | 0.1 | 0.3 | 1 | 3 | 0 | 0.3 | 1 | 3 | 10 |
| Compound of: | | | | | | | | | | |
| Example 15 | + | + | − | − | − | + | ± | − | − | |
| Example 16 | + | | ± | − | | + | + | − | − | |

The results shown in Table 4 revealed that the compounds of this invention are effective to inhibit platelet aggregation induced by B16 or 3LL cells both in in vitro and ex vivo testings and are expected to prevent metastasis of cancers.

TEST EXAMPLE 5

Test of Influence on Circulatory System 5 or 6 male normal SLC-Wistar rats per group (body weight: 205-255 g) orally received 50 mg/Kg of the test compound, and the blood pressure (tail cuff method) and the heart beats were measured with the passage of time in order to elucidate influences of the test compound on the circulatory system. The results obtained are shown in Table 5.

TABLE 5

| Test Compound | Compound of Example 21 | BL-3459 | BL-4162 |
|---|---|---|---|
| Initial Blood Pressure (mmHg) | 132 ± 2.5 | 129 ± 2.4 | 130 ± 3.2 |
| Reduction in Blood Pressure (%) | | | |
| Time After Admin. (hr) | | | |
| 1 | 1.0 | 23** | 11* |
| 2 | 5.0 | 28** | 16* |
| 3 | 5.0 | 26** | 17** |
| 4 | | | 14** |
| 5 | 5.0 | 34** | 14** |
| 6 | 1.0 | 35** | 13* |
| 24 | | 12* | |
| Initial Heart Beat (beat/min) | 381 ± 10 | 464 ± 10.3 | 377 ± 13.9 |
| Increase in Heart Beat (%) | | | |
| Time After Admin. (hr) | | | |
| 1 | 19** | 18** | 28** |
| 2 | 22** | 20** | 37** |
| 3 | 20** | 17** | 31** |
| 4 | | | 37** |
| 5 | 23** | 18** | 31** |
| 6 | 15** | 19* | 31** |

Note:
*P < 0.05
**P < 0.01

It can be seen from Table 5 that the compound of the present invention causes substantially no reduction in blood pressure and provokes only a relatively small increase in the heart beat. This indicates greatly reduced influences of the present compound upon the circulatory system as compared with the comparative compounds (BL-3459 & BL-4162).

As described in the foregoing the compounds according to the present invention have excellent water-solubility and platelet aggregation inhibitory activity and also reduced influences on the circulatory system.

In addition, it was confirmed that the compounds of this invention inhibit platelet aggregation induced by cancer cells and are expected for use as drugs for preventing metastasis of cancers.

TEST EXAMPLE 6

Test of Inhibitory Activity on Nucleoside Cyclic Monophosphate-Phosphodiesterase (PDE) of Human Platelets- or Heart-Origin Preparation of Phosphodiesterase and Assay of Its Activity Phosphodiesterase fractions were separated from 105,000×g of supernatant fractions from human platelets and heart by DEAE-cellulose column chromatography using the method of Timothy et al. (Arch. Biochem. Biophy. 196, 465–474, 1979) with minor modifications. These fractions were designated PDE I, PDE II and PDE III, depending upon the order of their emergence from the DEAE-cellulose column.

Phosphodiesterase activity was measured by the method of Thompson and Appleman (Biochemistry 10, 311–316, 1971) with slight modifications. The reaction mixture consisted of 25 mM of Tris-HCl (pH 7.4), 5 mM of $MgCl_2$, 1 μM of [$^3$H]-cAMP or cGMP (approximate 20,000 cpm), various concentrations of a test compound and the enzyme preparation. After incubation for 10 minutes at 30° C., the reaction was terminated by boiling the reaction mixture for 45 seconds. 5'-[$^3$H]-AMP or GMP formed by phosphodiesterase was converted to [$^3$H]adenosine or [$^3$H]quanosine by snake venom (Botherop Atrox) containing 5'-nucleotidase and the product isolated by a cation exchange resin was counted in a liquid scintillation counter. The results obtained are shown in Table 6.

TABLE 6

| | IC$_{50}$ (μM) | | | | | |
|---|---|---|---|---|---|---|
| | Platelet | | | Heart | | |
| Test Compound | PDE I (cGMP) | PDE II (cGMP) | PDE III (cAMP) | PDE I (cGMP) | PDE III (cAMP) | IC$_{50}$ Ratio (PDE II) Heart/Platelet |
| Example 21 | 70 | 57 | 1.3 | >100 | 1.4 | 1.1 |
| Example 15 | 3.9 | 5.1 | 0.063 | >100 | 0.11 | 1.7 |
| Example 5 | 45 | 57 | 0.35 | >50 | 0.8 | 2.3 |
| Example 22 | 1.6 | 2.9 | 0.15 | >100 | 0.18 | 1.2 |
| Example 16 | 30 | >30 | 0.0082 | >10 | 0.095 | 11.6 |
| 7-Piperidino Compound *1 | 93 | 54 | 0.15 | >100 | 0.8 | 5.3 |
| DH-6471 *2 | >100 | >100 | 0.065 | >10 | 0.46 | 7.1 |
| BL-4162 *3 | 3.9 | 3.3 | 0.013 | >10 | 0.096 | 7.4 |
| Amrinone *4 | >100 | Not Determined | 52 | >100 | 34 | 0.65 |

*1 Compound disclosed in Japanese Patent Application No. 111498/83 filed June 21, 1983 (corresponding to U.S. Pat. No. 74,031 filed June 21, 1984 by Fumiyoshi Ishikawa et al; Q-9366)
*2 Compound disclosed in U.S. Pat. No. 4,284,773
*3 Compound disclosed in U.S. Pat. No. 3,932,407
*4 5-Amino-(3,4'-bipyridin)-6(1H)—one (U.S. Pat. No. 4,004,012 and Merck Index, 10th Ed.)

As is apparent from the data shown in Table 6, Compound of Example 16 has high selectivity to platelet PDE and is expected to be very useful as platelet aggregation inhibitor. On the other hand, compounds of Examples 21, 15, 5 and 22 exhibit strong activity on heart PDE and therefore are expected to be useful as cardiotonic agent. These compounds also possess strong platelet aggregation inhibitory activity and can be used as platelet aggregation inhibitor unless the cardiotonic activity adversely affects the patients as side effect, for example, the patients not suffering from cardiac insufficiency and failure.

Compound of Example 16 has a low water-solubility and is mainly used by oral administration, whereas compounds of Examples 21, 15, 5 and 22 are water-soluble and can be advantageously used parenterally, for example, by intravenous administration.

The compounds (I) can be produced by reacting a compound represented by the formula (II):

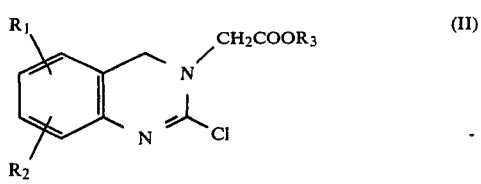

wherein $R_1$ and $R_2$ are as defined above; and $R_3$ represents a lower alkyl group having 1 to 6 carbon atoms, with ammonia.

The reaction can be advantageously carried out in a sealed tube in the presence of a solvent, such as a lower alcohol, e.g., methanol, ethanol, etc., at a temperature of from about 100° C. to about 150° C.

The compounds (I) can also be prepared by reacting a compound represented by the formula (III):

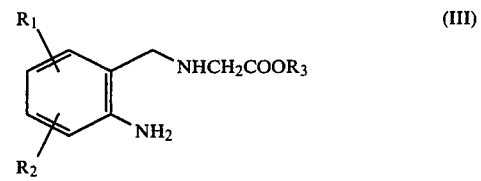

wherein $R_1$, $R_2$ and $R_3$ are as defined above, with a cyanogen halide, such as cyanogen bromide, or N-amidinopyrazole.

The above reaction can be advantageously carried out in a solvent, such as a lower alcohol, e.g., methanol, ethanol, etc., under reflux or at room temperature, followed by treating the reaction mixture with a weak base, such as sodium bicarbonate, sodium carbonate, etc.

The compounds of the formula (I) wherein $R_2$ is a hydrogen atom may also be prepared by catalytically reducing a compound represented by the formula (IV):

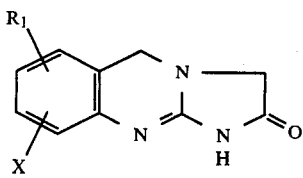

wherein $R_1$ is as defined above, and X represents a halogen atom, in a known manner, for example, in a solvent such as a lower alcohol, e.g., methanol, ethanol, etc., or water or a mixture thereof using a catalyst comprising metal palladium, etc.

The compounds (I) or their tautomers can be converted into the pharmaceutically acceptable salts, if necessary, e.g., hydrochlorides, hydrobromides, sulfates, phosphates, alkyl- or arylsulfonates, fumarates, maleates, succinates, citrates and the like.

The starting compounds of the formulae (II) and (III) can be prepared in accordance with the following reaction schem:

with ordinary pharmaceutically acceptable carriers selected depending on the type of dosage forms.

Suitable carriers which can be used are, for example, water, gelatin, gum arabic, lactose, starch, magnesium stearate, calcium hydrogenphosphate, talc, vegetable oils, polyalkylene glycols and the like.

Various dosage forms of the therapeutic agents can be selected according to the purpose of the therapy. Typical dosage forms which can be used include tablets, capsules, powders, liquid preparations, suspensions and injectable preparations (solutions, suspensions, etc.).

The compounds of this invention and their salts can preferably be administered orally or through intravenous injection. The dosage is usually about 1 mg to 20 mg per adult human per day in oral administration or about 0.1 mg to 10 mg per adult human per day in intravenous administration.

The present invention will further be illustrated in greater detail with reference to Reference Examples, Examples and Formulation Examples, but they are not to be construed as limiting the present invention.

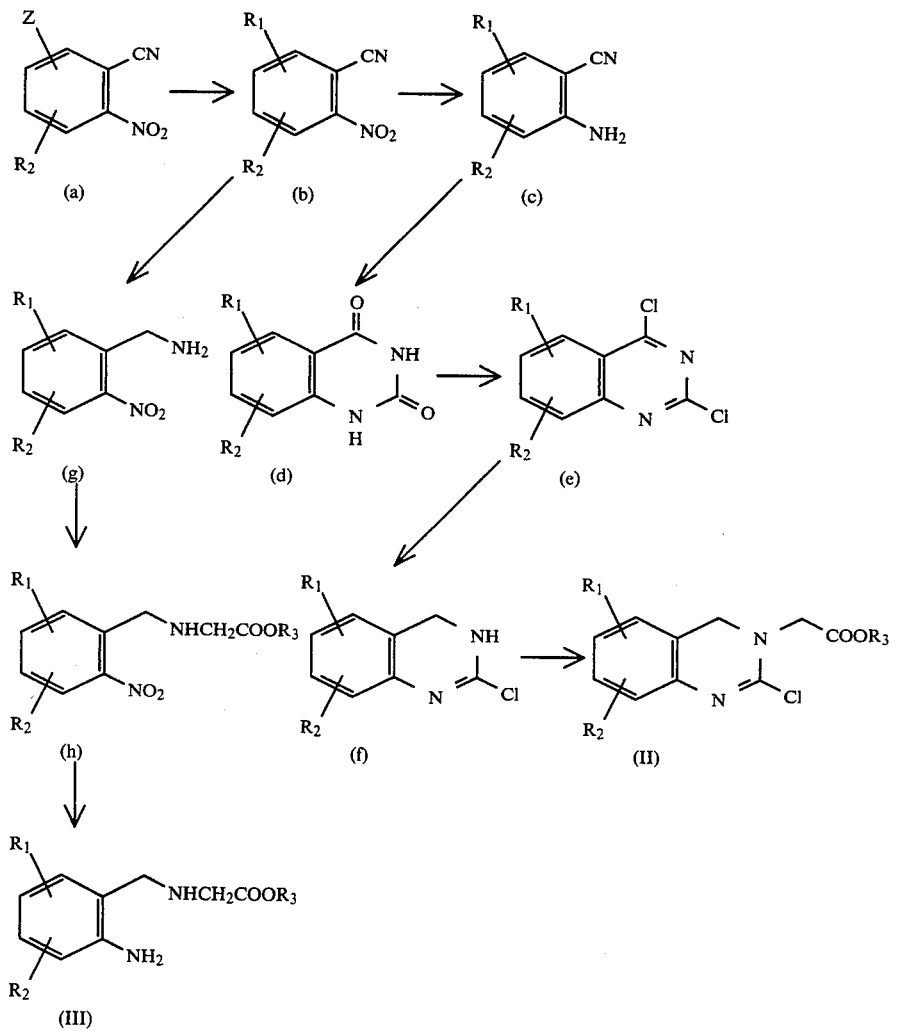

wherein $R_1$, $R_2$ and $R_3$ are as defined above; and Z represents a halogen atom or a nitro group.

In using the compounds of this invention or the salts thereof as therapeutic agents, these compounds can be formulated into pharmaceutical compositions together

REFERENCE EXAMPLE 1

(a) 5.8 g of 2,6-dinitrobenzonitrile was dissolved in 30 ml of dimethylformamide, and 10.2 ml of piperidine was added to the solution. The mixture was stirred at 50° C.

for 30 minutes while externally cooling because of heat generation. The reaction mixture was poured into water, and the precipitate thus formed was collected, washed with water and then with methanol, and dried to obtain 6.7 of 2-nitro-6-piperidinobenzonitrile (melting point: 122°–123° C.).

(b) 5.8 g of the above-obtained compound was added to a mixture of 40 ml of concentrated hydrochloric acid and 17.8 g of stannous chloride with stirring while externally cooling, followed by stirring at room temperature for 2 hours. The reaction mixture was poured into ice-water having dissolved therein 40 g of sodium hydroxide, and the precipitated crystals were extracted with chloroform. The extract was washed with water, dried and distilled off to remove the solvent. The residue was purified by silica gel chromatography to obtain 4.0 g of 2-amino-6-piperidinobenzonitrile as an oily substance.

(c) 4.0 g of the above-obtained compound was mixed with 8 g of urea, and the mixture was heated in an oil bath of 180° to 210° C. for 2.5 hours. After cooling, the reaction residue was pulverized and washed successively with water, acetone and diethyl ether. Then, the washed powder was added to 40 ml of concentrated hydrochloric acid and refluxed for 3 hours. After cooling, any insoluble matter was removed by filtration, and the filtrate was neutralized with aqueous ammonia to a pH of 7. The precipitate thus formed was filtered, washed successively with water and acetone, and dried to give 2.7 g of crude 5-piperidino-1,2,3,4-tetrahydroquinazoline-2,4-dione (melting point: above 280° C.).

(d) 2.7 g of the above-described compound was converted to its hydrochloride by treating with methanol-hydrochloric acid and added to 60 ml of phosphorus oxychloride. To the reaction mixture, 12 ml of N,N-diisopropylethylamine was added, and the resulting mixture was heat-refluxed for 18 hours. The reaction mixture was concentrated to dryness under reduced pressure, and the residue was poured into ice-water. The precipitate thus formed was filtered and extracted with chloroform. The extract was washed with water, dried, and concentrated to dryness under reduced pressure. The residue was purified by silica gel chromatography to give 2.6 g of 2,4-dichloro-5-piperidinoquinazoline as an oily substance.

(e) 2.6 g of the above prepared compound was dissolved in 25 ml of chloroform, and 25 ml of ethanol was added thereto. To the solution was further added 1.7 g of sodium borohydride while stirring. The stirring was continued for an additional 30 minutes at room temperature while externally cooling the heat generated. The reaction mixture was dried to a solid under reduced pressure, and water was added to the residue. The insoluble precipitate was collected by filtration, thoroughly washed with water and dried under reduced pressure to obtain 2.25 g of crude 2-chloro-5-piperidino-3,4-dihydroquinazoline as an amorphous powder. This product was used as it was as a starting material in Example 1.

REFERENCE EXAMPLE 2

(a) 13.0 g of 2,3-dichloro-6-nitrobenzonitrile was dissolved in 50 ml of dimethylformamide, and 11.0 g of pyrrolidine was added to the solution, followed by stirring while externally cooling because of heat generation. After continuing the stirring for 30 minutes, the reaction mixture was poured into water. The precipitate thus formed was filtered, washed with water and then with methanol to obtain 13.3 g of 2-chloro-6-nitro-3-pyrrolidinobenzonitrile (melting point: 170°–173° C.).

(b) 25 of the above-described compound was dissolved in 400 ml of dried tetrahydrofuran. To the resulting solution was introduced under a nitrogen steam diborane gas which was produced from 60 g of boron trifluoride ethyl etherate and 10 g of sodium borohydride in a usual manner, followed by stirring at room temperature for 5 hours. 190 ml of a 10% hydrochloric acid aqueous solution was added thereto portionwise, and stirring was continued for 2 hours. The tetrahydrofuran was removed by distillation under reduced pressure, and the aqueous layer was washed with chloroform, rendered alkaline with sodium hydrogencarbonate, and extracted with chloroform. The extract was washed with water, dried, and distilled off to remove the chloroform. The residue was purified by silica gel chromatography to yield 13.1 g of 2-chloro-6-nitro-3-pyrrolidinobenzylamine (melting point: 71°–73° C.).

(c) 6.5 g of the above-described compound and 1.4 g of sodium carbonate were added to 80 ml of dimethylformamide, and the mixture was heated at 80° C. while stirring. To the resulting mixture was added a solution of 4.27 g of ethyl bromoacetate in 60 ml of dimethylformamide, followed by stirring at that temperature for 3.5 hours. The reaction mixture was concentrated under reduced pressure, and the residue was dissolved in a 5% aqueous solution of sodium hydrogencarbonate and washed with benzene. The aqueous layer was made alkaline with aqueous ammonia and extracted with benzene. The extract was washed with water, dried and concentrated to dryness under reduced pressure. The residue was purified by silica gel chromatography to obtain 6.65 g of ethyl (2-chloro-6-nitro-3-pyrrolidinobenzyl)aminoacetate as an oily substance.

(d) 4.0 g of the above prepared compound was dissolved in 70 ml of ethanol, and 100 mg of platinum oxide was added thereto to effect catalytic reduction at room temperature under atmospheric pressure. After completion of the reaction, the catalyst was removed by filtration, and the filtrate was dried to a solid under reduced pressure. The residue was purified by silica gel chromatography to obtain 2.64 g of ethyl (6-amino-2-chloro-3-pyrrolidinobenzyl)aminoacetate (melting point: 69°–70° C.).

REFERENCE EXAMPLE 3

(a) 65 g of 5-chloro-2-nitrobenzonitrile was dissolved in 150 ml of dimethylformamide, and 150 ml of a 50% aqueous solution of dimethylamine was added thereto. After cooling the heat generated, the mixture was stirred at room temperature for 1 hour. The reaction mixture was poured into water, and the precipitate thus formed was collected by filtration, washed with water and then with methanol to obtain 64.5 g of 5-dimethylamino-2-nitrobenzonitrile (melting point: 174°–175° C.).

(b) A solution consisting of 120 ml of trifluoroacetic acid and 200 ml of tetrahydrofuran was added to a solution of 60 g of sodium borohydride in 300 ml of tetrahydrofuran under ice-cooling to a temperature of 15° C. or less. 63.4 of 5-dimethylamino-2-nitrobenzonitrile was added to the mixture, followed by stirring. After cooling the heat generated, the stirring was continued at room temperature overnight. 650 ml of a 10% aqueous solution of hydrochloric acid was then added thereto, followed by heat-refluxing for 1.5 hours. The tetrahydrofuran was removed by distillation under reduced pressure. The aqueous layer was washed with benzene, rendered alkaline with a sodium hydroxide aqueous solution, and extracted with chloroform. The extract was washed with water, dried and distilled off to remove the chloroform. The residue was purified by silica gel chromatography to obtain 33.4 g of 5-dimethylamino-2-nitrobenzylamine (melting point: 97°-98° C.).

(c) A mixture consisting of 33.4 g of the above-obtained compound, 9 g of sodium carbonate and 400 ml of dimethylformamide was heated to 80° C., and a solution of 28.2 g of ethyl bromoacetate in 500 ml of dimethylformamide was added thereto dropwise over a period of 2.5 hours. After the mixture was further stirred at 80° C. for an additional 2.5 hours, the dimethylformamide was removed by distillation under reduced pressure. The residue was dissolved in a 5% hydrochloric acid aqueous solution and washed with chloroform. The aqueous layer was made alkaline with ammonia and then extracted with benzene. The extract was washed with water, dried and distilled off to remove benzene. The residue was purified by silica gel chromatography to obtain 25.5 g of ethyl (5-dimethylamino-2-nitrobenzyl)aminoacetate (melting point: 70°-72° C.).

(d) 25.4 g of the above-described compound was dissolved in 800 ml of ethanol, and 5 g of 5% palladium-on-charcoal was added thereto to conduct catalytic reduction at room temperature. The catalyst was filtered, and the filtrate was distilled off under reduced pressure to obtain 21.8 g of crude ethyl (2-amino-5-dimethylaminobenzyl)aminoacetate.

EXAMPLE 1

1.9 g of 2-chloro-5-piperidino-3,4-dihydroquinazoline was dissolved in 50 ml of methylene chloride. 1.4 g of ethyl bromoacetate and 0.2 g of tetrabutylammonium iodide were added to the solution, and 7.5 ml of a 10N sodium hydroxide aqueous solution was further added thereto in a nitrogen stream while stirring. After stirring at room temperature for 1 hour, the reaction mixture was washed with water, dried, and distilled off under reduced pressure to obtain crude oily ethyl (2-chloro-5-piperidino-3,4-dihydroquinazolin-3-yl)acetate in a substantially quantitative yield. The crude product was added to 10 ml of a 10% ethanolic solution of ammonia and heated in a sealed tube at 120° to 130° C. for 4 hours. After cooling, crystals thus precipitated were collected by filtration, washed with water and dried to obtain 0.65 g of 6-piperidino-1,2,3,5-tetrahydroimidazo[2,1-b]quinazolin-2-one. This product was suspended in methanol and dissolved therein by adjusting the pH to 1 to 2 with concentrated hydrochloric acid. The solution was treated with activated carbon, followed by filtration. The filtrate was concentrated under reduced pressure, and the crystals thus precipitated were collected to obtain a hydrochloride (melting point: 242°-245° C. with decomposition).

IR$\nu_{max}^{KBr}$ cm$^{-1}$: 3320, 3100-2300, 1795, 1685, 1630, 1615, 1590.

$^1$H-NMR (D$_2$O)δ: 1.35-1.9 (6H, m), 2.6-2.95 (4H, m), 4.31 (2H, s), 4.66 (2H, s), 6.95-7.1 (2H, m), 7.34 (1H, t).

Elementary Analysis for C$_{15}$H$_{18}$N$_4$O.2HCl.2H$_2$O: Calcd.: C, 47.50%; H, 6.30%; N, 14.77%. Found: C, 47.39%; H, 5.99%; N, 14.81%.

EXAMPLES 2 TO 19

In the similar manner as described in Example 1, the compounds shown in Table 1 were obtained. The starting compounds used in these Examples were prepared in the similar manner as described in Reference Example 1.

TABLE 1

| Example No. | R$_1$ | R$_2$ | Decomp. point (°C.) | IR (cm$^{-1}$) | $^1$H—NMR (Solvent)(δ) | Molecular Formula Calcd. (%) Found (%) | | |
|---|---|---|---|---|---|---|---|---|
| | | | | | | C | H | N |
| 2 | 6-N(CH$_3$)$_2$ | H | 232-233 | 3350 3100-2400 1800 1685 1630 1615 1590 | (DMSO—d$_6$) 2.77(6H,s) 4.28(2H,s) 4.78(2H,s) 7.2-7.5(3H,m) | C$_{12}$H$_{14}$N$_4$O.2HCl.½H$_2$O 46.17 45.85 | 5.49 5.80 | 17.95 17.67 |
| 3 | 6-N(C$_2$H$_5$)$_2$ | H | 192-194 | 3395 3070-2400 1790 1690 1655 1585 | (DMSO—d$_6$) 0.95(6H,t) 2.9-3.3(4H,m) 4.27(2H,s) 4.72(2H,s) 7.1-7.6(3H,m) | C$_{14}$H$_{18}$N$_4$O.2HCl.H$_2$O 45.78 45.41 | 6.59 6.13 | 15.25 15.09 |
| 4 | 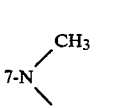 | H | 178-180 | 3380 3100-2200 1785 1680 1610 1605 1510 | (D$_2$O) 2.98(3H,s) 4.16(2H,s) 4.56(2H×2,s) 6.9-7.2(3H,m) 7.2(5H,s) | C$_{18}$H$_{18}$N$_4$O.2HCl.H$_2$O 54.42 54.14 | 5.58 5.65 | 14.10 13.84 |
| 5 | 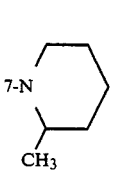 | H | unclear | 3400 3000-2600 1795 1680 1605 1510 | (D$_2$O) 1.08(3H,t) 1.65-2.3(6H,m) 2.95-3.15(3H,m) 4.36(2H,s) 4.86(2H,s) 7.29(1H,d) 7.42-7.65(2H,m) | C$_{16}$H$_{20}$N$_4$O.2HCl.H$_2$O 51.21 50.85 | 6.45 6.36 | 14.93 14.87 |

TABLE 1-continued

| Example No. | R₁ | R₂ | Decomp. point (°C.) | IR (cm⁻¹) | ¹H—NMR (Solvent)(δ) | Molecular Formula Calcd. (%) / Found (%) C | H | N |
|---|---|---|---|---|---|---|---|---|
| 6 | 8-N(piperidinyl) | H | 272-275 | 3420, 3400-2300, 1805 1695, 1655 1605, 1525 | (DMSO—d₆) 1.45-2.2(6H,m) 3.25-3.6(4H,m) 4.28(2H,s) 4.69(2H,s) 7.25-7.75(3H,m) | $C_{15}H_{18}N_4O.2HCl.H_2O$ 49.87 / 49.25 | 6.14 / 6.25 | 15.51 / 15.32 |
| 7 | 8-N(2,6-dimethylpiperidinyl) | H | 262-264 | 3410, 3100-2300, 1790 1685, 1610 | (DMSO—d₆) 0.93(6H,d) 1.6-2.4(4H,m) 2.74(2H,t) 3.35-3.65(2H,m) 4.27(2H,s) 4.67(2H,s) 7.25-7.55(3H,m) | $C_{17}H_{22}N_4O.2HCl.H_2O$ 52.45 / 52.45 | 6.73 / 6.74 | 14.39 / 14.22 |
| 8 | 8-N(morpholinyl) | H | >280 | 3420, 3150-2000, 1790 1765, 1630 1600 | (DMSO—d₆) 2.95-3.2(4H,m) 2.64(4H,m) 4.24(2H,s) 4.57(2H,s) 6.9 (2H,m) 7.10(1H,d) | $C_{14}H_{16}N_4O_2.2HCl.\frac{1}{2}H_2O$ 47.47 / 47.64 | 5.41 / 5.43 | 15.82 / 15.86 |
| 9 | 7-N(piperidinyl) | 6-Cl | 235-237 | 3350, 2650(br s), 1800 1785, 1600 1630, 1590 | (TFA) 2.29(6H,m) 3.90(4H,m) 4.61(2H,s) 5.02(2H,s) 7.40(1H,d) 7.86(1H,d) | $C_{15}H_{17}ClN_4O.2HCl.2H_2O$ 43.55 / 43.63 | 5.60 / 5.35 | 13.54 / 13.44 |
| 10 | 7-N(2-methylpiperidinyl) | 6-Cl | >280 | 3400, 2950-2600, 1790 1680, 1630 1590, 1485 | (DMSO—d₆-D₂O) 0.84(3H,d) 1.6 (6H,m) 3.0-3.5(1H,m) 4.28(2H,s) 4.68(2H,s) 7.18(1H,d) 7.37(1H,d) | $C_{16}H_{10}ClN_4O.2HCl.3/2 H_2O$ 45.89 / 46.02 | 5.78 / 5.17 | 13.38 / 13.35 |
| 11 | 7-N(4-methylpiperidinyl) | 6-Cl | 240-245 | 3400, 2900-2600, 1760 1680, 1630 1590, 1490 | (TFA) 1.22(3H,br s) 2.0-2.4(5H,m) 3.95(4H,m) 4.63(2H,s) 5.06(2H,s) 7.45(1H,d) 7.86(1H,d) | $C_{16}H_{19}ClN_4O.2HCl.H_2O$ 46.90 / 46.95 | 5.66 / 5.54 | 13.67 / 13.71 |
| 12 | 7-N(2,6-dimethylpiperidinyl) | 6-Cl | 265-280 | 3350, 2900-2600, 1790 1680, 1625 1490 | (DMSO—d₆) 0.87(6H,d) 1.8 (4H,m) 2.16(2H,t) 3.13(2H,m) 4.26(2H,s) 4.65(2H,s) 7.13(1H,d) 7.24(1H,d) | $C_{17}H_{21}ClN_4O.2HCl.H_2O$ 48.18 / 48.43 | 5.95 / 6.11 | 13.22 / 12.80 |
| 13 | 8-N(CH₃)₂ | 6-Cl | >280 | 3400, 3150-2450, 2350 1785, 1690 1630, 1595 | (DMSO—d₆) 2.92(6H,s) 3.17(3H,s) 4.27(2H,s) 4.54(2H,s) 6.62(2H,s) | $C_{12}H_{13}ClN_4O.2HCl.CH_3OH$ 42.24 / 42.28 | 5.18 / 5.05 | 15.16 / 15.01 |
| 14 | 8-N(piperidinyl) | 6-Cl | >280 | 3700-3100, 3100-2400, 1780 1690, 1630 1610 | (DMSO—d₆) 1.60(6H,m) 3.17(3H,s) 3.24(4H,m) 4.27(2H,s) 4.57(2H,s) 7.03(2H,s) | $C_{15}H_{17}ClN_4O.2HCl.H_2O.CH_3OH$ 44.93 / 45.54 | 5.89 / 5.44 | 13.10 / 12.60 |
| 15 | 7-N(CH₃)₂ | 8-Cl | 280-282 | 3300 | (D₂O) | $C_{12}H_{13}ClN_4O.2HCl.2H_2O$ | | |

TABLE 1-continued

| Example No. | R₁ | R₂ | Decomp. point (°C.) | IR (cm⁻¹) | ¹H—NMR (Solvent)(δ) | Molecular Formula Calcd. (%) Found (%) C | H | N |
|---|---|---|---|---|---|---|---|---|
| | | | | 2650(br s) 1780 1680 1635 1500 | 3.34(6H,s) 4.36(2H,s) 4.87(2H,s) 7.40(1H,s) 7.74(1H,s) | 38.57 38.52 | 5.12 4.87 | 14.99 14.82 |
| 16 | 7-N⟨hexyl⟩ | 8-Cl | 185–187 | 3440 2650(br s) 1800–1680 1640 1615 1595 | (D₂O) 1.7–2.4(6H,m) 3.75–3.95(4H,m) 4.51(2H,s) 5.02(2H,s) 7.80(1H,s) 7.52(1H,s) | $C_{15}H_{17}ClN_4O \cdot 2HCl \cdot H_2O$ 45.53 45.10 | 5.35 5.37 | 14.16 14.08 |
| 17 | 7-N⟨morpholino⟩ | 8-Cl | 269–270 | 3400–2450 1790 1680 1630 1580 | (DMSO—d₆) 2.65–2.8(4H,m) 2.85–3.0(4H,m) 4.22(2H,s) 4.64(2H,s) 7.10(1H,s) 7.36(1H,s) | $C_{14}H_{15}ClN_4O_2 \cdot HCl \cdot \tfrac{1}{2}H_2O$ 47.74 48.21 | 4.86 5.01 | 15.91 15.64 |
| 18 | 7-N⟨hexyl⟩ | 8-CH₃ | 200 | 3380 2900–2200 1780 1680 1610 1590 | (D₂O) 1.6–2.2(6H,m) 2.50(3H,s) 3.69(4H,m) 4.37(2H,s) 4.84(2H,s) 7.16(1H,s) 7.58(1H,s) | $C_{16}H_{20}N_4O \cdot 2HCl \cdot H_2O$ 50.01 50.09 | 6.56 6.68 | 14.58 14.59 |
| 19 | 7-N⟨hexyl⟩ | 8-OCH₃ | unclear | 3370 3000–2600 1785 1680 1600 | (D₂O) 1.5–2.2(6H,m) 1.20(t) 3.5–3.7(4H,m) 3.86(q) 4.00(3H,s) 4.36(2H,s) 4.78(2H,s) 7.52(1H,s) 7.90(1H,s) | $C_{16}H_{20}N_4O_2 \cdot 2HCl \cdot H_2O \cdot \tfrac{1}{2}C_2H_5OH$ 49.28 49.80 | 6.57 6.45 | 13.52 13.53 |

EXAMPLE 20

2.6 g of ethyl (6-amino-2-chloro-3-pyrrolidinobenzyl)aminoacetate was dissolved in 50 ml of ethanol, and a solution of 0.88 g of cyanogen bromide in 5 ml of ethanol was added to the solution, followed by stirring at room temperature for 16 hours. The reaction mixture was adjusted to a pH of 8 to 9 with a saturated aqueous solution of sodium hydrogencarbonate, and the stirring was continued for an additional one hour. Adjustment to a pH of 10 with a 2N sodium hydroxide aqueous solution precipitated crystals, which were then collected by filtration, washed with water and dried to obtain 2.2 g of a free base of 6-chloro-7-pyrrolidino-1,2,3,5-tetrahydroimidazo[2,1-b]quinazolin-2-one. This product was converted to its hydrochloride in a usual manner (melting point: 233° C. with decomposition).

IR$\nu_{max}^{KBr}$ cm⁻¹: 3320, 2800, 1450, 1790, 1680, 1590.

¹H-NMR (DMSO-d₆)δ: 1.92 (4H, m), 3.33 (4H, m), 4.30 (2H, s), 4.66 (2H, s), 7.12 (1H, d), 7.29 (1H, d).

Elementary Analysis for C₁₄H₁₅ClN₄O: Calcd.: C, 44.06; H, 5.02; N, 14.08(%). Found: C, 44.34; H, 5.10; N, 14.62(%).

EXAMPLE 21

21.0 g of ethyl (2-amino-5-dimethylaminobenzyl)aminoacetate was dissolved in 200 ml of ethanol, and a solution of 8.8 g of cyanogen bromide in 60 ml of ethanol was added thereto, followed by stirring at room temperature overnight. To the reaction mixture was added a saturated aqueous solution of sodium hydrogen-carbonate, followed by stirring for 30 minutes. The stirring was further continued at 60° C. for an additional one hour, and the precipitate thus formed was collected by filtration, washed with water and dried to obtain 13.3 g of a free base of 7-dimethylamino-1,2,3,5-tetrahydroimidazo[2,1-b]quinazolin-2-one. The product was then treated with methanol-hydrochloric acid to form a dihydrochloride (melting point: 250°–252° C. with decomposition).

IR$\nu_{max}^{KBr}$ cm⁻¹: 3500, 3200, 3020–2300, 1790, 1770, 1680.

¹H-NMR (D₂O)δ: 3.34 (6H, s), 4.42 (2H, s), 4.94 (2H, s), 7.31 (1H, d), 7.58 (2H, dd).

Elementary Analysis for C₁₂H₁₄N₄O·2HCl·0.5H₂O: Calcd.: C, 46.17; H, 5.49; N, 17.95 (%). Found: C, 46.58; H, 5.42; N, 17.78 (%).

EXAMPLES 22 TO 25

In the same manner as described in Example 20, the compounds shown in Table 2 were obtained. The starting compounds used in these Examples were prepared according to the method as described in Example 20.

TABLE 2

| Example No. | $R_1$ | $R_2$ | Decomp. point (°C.) | IR (cm$^{-1}$) | $^1$H—NMR (Solvent)(δ) | Molecular Formula Calcd. (%) Found (%) | | |
|---|---|---|---|---|---|---|---|---|
| | | | | | | C | H | N |
| 22 | 7-N(CH$_3$)$_2$ | 6-Cl | 186–188 | 3460 3210 2900–2400 1780 1670 1590 1480 | (D$_2$O) 3.38(6H,s) 4.41(2H,s) 4.88(2H,s) 7.28(1H,d) 7.83(1H,d) | C$_{12}$H$_{13}$ClN$_4$O.2HCl.H$_2$O 40.53 40.33 | 4.82 4.92 | 15.75 15.60 |
| 23 | 7-N(C$_2$H$_5$)$_2$ | 6-Cl | 223–225 | 3300 3050–2650 1790 1690 1600 1500 | (D$_2$O) 1.2 (6H,t) 3.83(4H,q) 4.51(2H,s) 4.98(2H,s) 7.41(1H,d) 7.81(1H,d) | C$_{14}$H$_{17}$ClN$_4$O.2HCl.½H$_2$O 44.88 44.86 | 5.38 5.67 | 14.95 14.83 |
| 24 | 7-N⟨⟩N—CH$_3$ | 6-Cl | 229–232 | 3400 2840 2600(br s) 1790 1680 1620 1480 | (DMSO—d$_6$) 2.22(3H,s) 2.5 (4H,m) 2.86(4H,m) 3.67(2H,s) 4.43(2H,s) 6.68(1H,d) 7.01(1H,d) | C$_{15}$H$_{18}$ClN$_5$O.2HCl 41.98 41.56 | 4.93 5.62 | 16.32 15.98 |
| 25 | 8-N⟨⟩ | 7-CH$_3$ | unclear | 3450 3000–2650 1780 1690 1800 | (D$_2$O) 1.9 (2H,m) 2.15(4H,m) 2.53(3H,s) 3.73(4H,m) 4.38(2H,s) 4.85(2H,s) 7.35(2H,s) | C$_{16}$H$_{20}$N$_4$O.2HCl.½H$_2$O 52.47 52.90 | 6.33 6.59 | 15.30 14.96 |

EXAMPLE 26

1.5 g of 6-chloro-7-pyrrolidino-1,2,3,5-tetrahydroimidazo[2,1-b]quinazolin-2-one dihydrochloride was dissolved in 50 ml of methanol and catalytically reduced in the presence of 250 mg of 10% palladium-on-charcoal at ambient temperature under atmospheric pressure. After completion of the reaction, the catalyst was removed by filtration, and the filtrate was dried to a solid under reduced pressure to obtain 0.84 g of 7-pyrrolidino-1,2,3,5-tetrahydroimidazo[2,1-b]quinazolin-2-one dihydrochloride (melting point: above 280° C.).
IR$\nu_{max}^{KBr}$ cm$^{-1}$: 3400, 2800, 1800, 1670, 1600, 1510.
$^1$H-NMR (DMSO-d$_6$)δ: 2.37 (4H, m), 3.88 (4H, m), 4.45 (2H, s), 4.93 (2H, s), 7.35 (1H, d), 7.54 (2H, m).

Elementary Analysis for C$_{14}$H$_{16}$N$_4$O.2HCl.H$_2$O: Calcd.: C, 48.43; H, 5.81; N, 16.13(%). Found: C, 48.90; H, 5.90; N, 16.16(%).

EXAMPLES 27 AND 28

In the similar manner as described in Example 26, the compound shown in Table 3 were obtained. The starting compounds used in Examples 27 and 28 are the compounds as obtained in Examples 11 and 17, respectively.

TABLE 3

| Example No. | $R_1$ | $R_2$ | Decomp. point (°C.) | IR (cm$^{-1}$) | $^1$H—NMR (Solvent)(δ) | Molecular Formula Calcd. (%) Found (%) | | |
|---|---|---|---|---|---|---|---|---|
| | | | | | | C | H | N |
| 27 | 7-N⟨⟩—CH$_3$ | H | 170–180 | 3300 3050–2500 1790 1680 1605 1510 | (D$_2$O) 1.10(3H,br s) 1.6–2.3(5H,m) 3.7 (4H,m) 4.45(2H,s) 4.96(2H,s) 7.35(1H,d) 7.64(2H,m) | C$_{16}$H$_{20}$ON$_4$O.2HCl.3/2H$_2$O 50.01 49.80 | 6.56 6.19 | 14.58 13.92 |
| 28 | 7-N⟨⟩O | H | >280 | 3400 2650(br s) 1795 1665 1590 1495 | (D$_2$O) 3.7–3.9(4H,m) 4.1–4.3(4H,m) 4.45(2H,s) 4.94(2H,s) 7.36(1H,d) 7.60(1H,d) 7.67(1H,dd) | C$_{14}$H$_{16}$N$_4$O.2HCl.2H$_2$O 44.11 43.97 | 5.82 5.72 | 14.70 14.49 |

FORMULATION EXAMPLE 1

The following components were blended, granulated and punched out to prepare tablets each weighing 100 mg.

| | |
|---|---|
| 8-Chloro-7-piperidino-1,2,3,5-tetra-hydroimidazo[2,1-b]quinazolin-2-one dihydrochloride monohydrate | 30 mg |
| Lactose | 626 mg |
| Corn starch | 300 mg |
| Hydroxypropyl cellulose | 40 mg |
| Magnesium stearate | 4 mg |
| Total: | 1,000 mg |

FORMULATION EXAMPLE 2

300 mg of 7-dimethylamino-1,2,3,5-tetrahydroimidazo[2,1-b]quinazolin-2-one dihydrochloride semihydrate and 1.0 g of D-mannitol were dissolved in distilled water for injection to make 100 ml. The solution was filtered using a membrane filter of 0.2μ, placed in vials in 1.0 ml portions, freeze-dried, and sealed to prepare freeze-dried preparations.

While the invention has been described in detail and with reference to specific embodiments thereof, it will be apparent to one skilled in the art that various changes and modifications can be made therein without departing from the spirit and scope thereof.

What is claimed is:

1. An imidazoquinazolin-2-one compound represented by the formula (I):

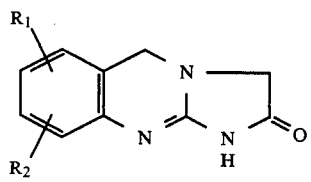

(I)

wherein $R_1$ represents a di-lower alkylamino group having 1 to 6 carbon atoms in its alkyl moiety, an unsubstituted or substituted cyclic amino group selected from the group of a 1-pyrrolidinyl group, a 1-piperidinyl group, a 1-piperazinyl group and a 4-morpholinyl group, and wherein said cyclic amino group can be substituted by 1 or 2 lower alkyl groups; and $R_2$ represents a hydrogen atom, a halogen atom, a lower alkyl group having 1 to 6 carbon atoms or a lower alkoxy group having 1 to 6 carbon atoms, with proviso that the compound wherein $R_1$ is a 7-piperidino group and $R_2$ is a hydrogen atom is excluded, and a pharmaceutically acceptable salt thereof.

2. An imidazoquinazoline compound as claimed in claim 1, wherein the cyclic amino group is a 1-pyrrolidinyl group, a 1-piperidinyl group, a 1-piperazinyl group or a 4-morpholinyl group, and the substituted cyclic amino group is a 4-methyl-1-piperazinyl group, a 4-methyl-1-piperidinyl group, a 2-methyl-1-piperidinyl group or a 3,5-dimethyl-1-piperidinyl group.

3. An imidazoquinazolin-2-one compound according to claim 1, wherein $R_1$ is a 7-dimethylamino group and $R_2$ is hydrogen.

4. An imidazoquinazolin-2-one compound according to claim 1, wherein $R_1$ is a 7-dimethylamino group and $R_2$ is 8-chloro.

5. An imidazoquinazolin-2-one compound according to claim 1, wherein $R_1$ is a 7-dimethylamino group and $R_2$ is 6-chloro.

6. An imidazoquinazolin-2-one compound according to claim 1, wherein $R_1$ is a 7-(4-methyl-1-piperazinyl) group and $R_2$ is 6-chloro.

7. An imidazoquinazolin-2-one compound according to claim 1, wherein $R_1$ is a 7-(1-piperazinyl) group and $R_2$ is 8-chloro.

8. An platelet aggregation inhibitor comprising a platelet aggregation inhibiting effective amount of an imidazoquinazolin-2-one compound represented by formula (I):

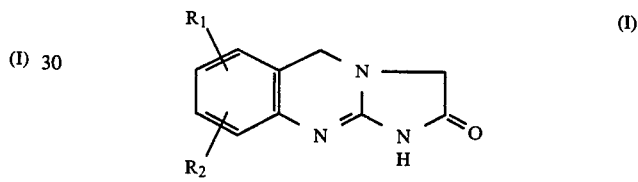

(I)

wherein $R_1$ represents a di-lower alkylamino group having 1 to 6 carbon atoms in its alkyl moiety, an unsubstituted or substituted cyclic amino group; selected from the group consisting of a 1-pyrrolidinyl group, a 1-piperidinyl group, a 1-piperazinyl group and a 4-morpholinyl group, and wherein said cyclic amino group can be substituted by 1 or 2 lower alkyl groups; and $R_2$ represents a hydrogen atom, a halogen atom, a lower alkyl group having 1 to 6 carbon atoms or a lower alkoxy group having 1 to 6 carbon atoms, with proviso that the compound wherein $R_1$ is a 7-piperidino group and $R_2$ is a hydrogen atom is excluded, or a pharmaceutically-acceptable salt thereof as an active ingredient, and a pharmaceutically-acceptable carrier.

* * * * *